(12) United States Patent
Gozen et al.

(10) Patent No.: US 11,523,769 B2
(45) Date of Patent: Dec. 13, 2022

(54) GARMENT AND METHOD FOR MEASURING HUMAN MILK PRODUCTION AND BREASTFEEDING PARAMETERS

(71) Applicant: Washington State University, Pullman, WA (US)

(72) Inventors: Bulent Arda Gozen, Pullman, WA (US); Michelle Kay McGuire, Moscow, ID (US); Abhishek Gannarapu, Pullman, WA (US); Kimberly Ann Lackey, Pullman, WA (US); Tyler Nelson Meine, Pullman, WA (US); Dallas Daaren Chang, Bothell, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 314 days.

(21) Appl. No.: 16/617,590

(22) PCT Filed: May 31, 2018

(86) PCT No.: PCT/US2018/035405
§ 371 (c)(1),
(2) Date: Nov. 27, 2019

(87) PCT Pub. No.: WO2018/222879
PCT Pub. Date: Dec. 6, 2018

(65) Prior Publication Data
US 2020/0100721 A1    Apr. 2, 2020

Related U.S. Application Data

(60) Provisional application No. 62/658,791, filed on Apr. 17, 2018, provisional application No. 62/513,630, filed on Jun. 1, 2017.

(51) Int. Cl.
| | | |
|---|---|---|
| A61B 5/00 | (2006.01) | |
| A61B 5/01 | (2006.01) | |
| A61B 5/08 | (2006.01) | |
| A61B 5/107 | (2006.01) | |

(52) U.S. Cl.
CPC .............. *A61B 5/4312* (2013.01); *A61B 5/01* (2013.01); *A61B 5/08* (2013.01); *A61B 5/1073* (2013.01); *A61B 5/6804* (2013.01); *A61B 2562/0261* (2013.01); *A61B 2562/0271* (2013.01)

(58) Field of Classification Search
CPC ........... A61B 5/4312; A61B 5/01; A61B 5/08; A61B 5/1073; A61B 5/6804; A61B 2562/0261; A61B 2562/0271; G01F 17/00; A01J 5/01
USPC ........................................................ 600/587
See application file for complete search history.

(56) References Cited

U.S. PATENT DOCUMENTS 4,338,953 A  *  7/1982  Ward .................... A61B 5/1073
                                                          33/512
5,827,191 A     10/1998  Rosenfeld
5,830,159 A  *  11/1998  Netta ..................... A61B 5/015
                                                          600/587

(Continued)

*Primary Examiner* — May A Abouelela
(74) *Attorney, Agent, or Firm* — WCF IP

(57) ABSTRACT

Devices and methods for simultaneously measuring, in real time: 1) volumetric changes of a mammalian breast due to milk production and output, and 2) breast temperature, are provided. The devices are generally sensors which can be disposed within a wearable garment such as a bra.

7 Claims, 15 Drawing Sheets

(56) References Cited

U.S. PATENT DOCUMENTS

| | | | |
|---|---|---|---|
| 7,250,775 B1 | 7/2007 | Collins et al. | |
| 7,896,835 B2* | 3/2011 | Dahan | G01F 1/72 |
| | | | 604/76 |
| 8,114,030 B2* | 2/2012 | Ales | A61B 5/103 |
| | | | 600/584 |
| 8,801,658 B2* | 8/2014 | Harari | A61B 5/1075 |
| | | | 604/74 |
| 8,992,445 B2* | 3/2015 | Blondheim | A61B 5/4878 |
| | | | 600/587 |
| 9,211,366 B1* | 12/2015 | Gutwein | A61B 5/103 |
| 9,616,156 B2* | 4/2017 | Alvarez | A61M 1/066 |
| 9,623,160 B2* | 4/2017 | Alvarez | A61M 1/06 |
| 10,617,805 B2* | 4/2020 | Gaskin | A61M 1/062 |
| 10,667,742 B2* | 6/2020 | Goodall | A61B 5/0022 |
| 10,772,507 B2* | 9/2020 | Goodall | A61B 5/1073 |
| 10,912,511 B2* | 2/2021 | Melamed | A61B 5/7405 |
| 11,089,991 B2* | 8/2021 | Makower | A61M 1/06 |
| 2005/0059928 A1 | 3/2005 | Larsson | |
| 2008/0039741 A1 | 2/2008 | Shemesh et al. | |
| 2008/0077040 A1* | 3/2008 | Ales | A61B 5/4238 |
| | | | 600/546 |
| 2008/0077042 A1* | 3/2008 | Feldkamp | A61B 5/103 |
| | | | 600/547 |
| 2008/0097169 A1* | 4/2008 | Long | A61B 5/4312 |
| | | | 600/301 |
| 2009/0287119 A1* | 11/2009 | Chapman | A61B 5/4312 |
| | | | 600/587 |
| 2010/0217148 A1 | 8/2010 | Binder | |
| 2012/0004603 A1* | 1/2012 | Harari | A61B 5/1075 |
| | | | 604/74 |

* cited by examiner

GARMENT AND METHOD FOR MEASURING HUMAN MILK PRODUCTION AND BREASTFEEDING PARAMETERS

CROSS-REFERENCE TO RELATED APPLICATIONS

This application claims benefit of U.S. provisional patent applications 62/513,630, filed Jun. 1, 2017, and 62/658,791 filed Apr. 17, 2018, the complete contents of each of which is hereby incorporated by reference.

BACKGROUND OF THE INVENTION

Field of the Invention

The invention generally relates to devices and methods for simultaneously measuring, in real time: 1) volumetric changes of a mammalian breast due to milk production and output and 2) breast temperature. In particular, the invention provides a wearable garment comprising embedded conductive material capable of detecting volumetric changes in and the temperature of a circumscribed area such as a breast.

Description of Related Art

Milk production output during lactation is a critical parameter for infant nutrition and growth. The methods primarily used for measuring of milk output have been stable isotope techniques [1] and/or 24-hour infant weighback protocols [2]. However, these methods are inconvenient, difficult to implement and provide slow and low resolution measurements. To address these challenges, several devices integrated onto the mother's breast have been proposed for direct measurement of milk flow (see U.S. Pat. No. 8,280,493) or detection of the changes of the bioimpedance signals due to milk flow (U.S. patent application Ser. No. 12/776,023; International PCT patent application WO2018053045). Even though such approaches provide accurate measurements, their invasive nature prevents their broader application.

One particular measure that can be used for non-invasive determination of milk output is variation of the breast volume during lactation. Non-contact topological measurements of the breast before and after a breastfeeding bout through 3D-scanning is one way to realize accurate but discontinuous measurements of breast volume [6]. However, this method requires sophisticated equipment and inconvenient visits to a facility with the equipment.

In addition, Harari et al. have proposed a wearable device capable of quantifying breast volume through monitoring of a supplementary fluid pressure (U.S. Pat. No. 8,801,658). However, the device requires significant manipulation of a pumping device prior to and after use, which discourages adoption of the technology.

Despite these advances, a technology that is simultaneously (1) non-invasive, (2) accurate, and (3) fully quantitative, (4) does not require additional materials and material control systems and (5) can be used continuously during lactation, and that (6) is convenient and "user friendly", has not emerged. Further, in addition to the challenge of measuring milk output, there exist a number of other parameters, the measurement of which is critical for maternal and infant health, including infant suckling frequency and mechanics along with breast temperature. None of the aforementioned approaches can simultaneously monitor these parameters while also measuring milk output.

The application of liquid conductor-based sensors has been demonstrated for measurement of gait [8] and hand motions [9]. However, those applications have been limited to highly localized sensing of uni-axial deformations.

SUMMARY OF THE INVENTION

Provided herein is the first smart wearable electronic device capable of sensing volumetric changes of the mammalian (e.g. human) breast due to milk production and output, as well as breast temperature, in real time. The device is convenient and "user friendly" so that nursing mothers are likely to adopt the technology. The device comprises intrinsic electrically conductive liquids (e.g. non-volatile conductive liquids) embedded in a soft elastomeric material that conforms to solid or semisolid surfaces with which it is in contact, e.g. a surface of a breast. Once positioned on a surface, the conductors flow and deform in response to changes in and movement of the underlying surface on which the material is placed. For example, the conductors respond to local deformations such as expansion, contraction, positional changes, etc. Conductivity is detected while the device is worn, (e.g. before, during and after nursing), and fluctuations in the electrical properties of the conductors, which correlate with the changes/movements, are detected, measured and quantified. The measurements are used to calculate and monitor, for example, changes in breast volume during and in between nursing sessions.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide a sensor comprising: a closed band of non-conductive elastomeric material having at least one enclosed channel embedded therein, wherein at least one enclosed channel is filled with a non-volatile electrically conductive liquid; at least two microelectrodes in electrical communication with the non-volatile electrically conductive liquid; and a connector which transmits and receives electrical signals to and from the at least two microelectrodes and an external electronics system. In some aspects, the sensor further comprises a temperature sensor. In additional aspects, the external electronics system comprises an electronic device capable of performing signal processing.

The invention also provides a wearable garment for monitoring breast volume and temperature, comprising at least one cup having a contoured shape for engaging a woman's breast, wherein at least one cup comprises at least one sensor according to any of claims 1-3. In some aspects, one cup of the wearable garment comprises a sensor according to any of claim 1-3 and a second cup of the wearable garment comprises a control sensor that detects inhalation and exhalation.

The invention also provides a method of measuring breast volume and temperature in a subject in need thereof, comprising, positioning a sensor of claim 1 or a wearable garment of claim 4 on a breast or breasts of the subject, measuring sensor impedance as a function of frequency to obtain a frequency response, determining circuit component values by fitting the frequency response with a circuit model that represents sensor behavior, and calculating breast volume and temperature using the circuit component values and predetermined calibration functions that correlate the circuit component values to corresponding physical variables for breast volume and temperature. In some aspects, the predetermined calibration functions are obtained by measuring sensor frequency responses at a plurality of breast volume and temperature levels. This calibration can be done on an "artificial" or "mock" breast in a testing facility, prior to use of the device by women.

DETAILED DESCRIPTION

Figure 1A:
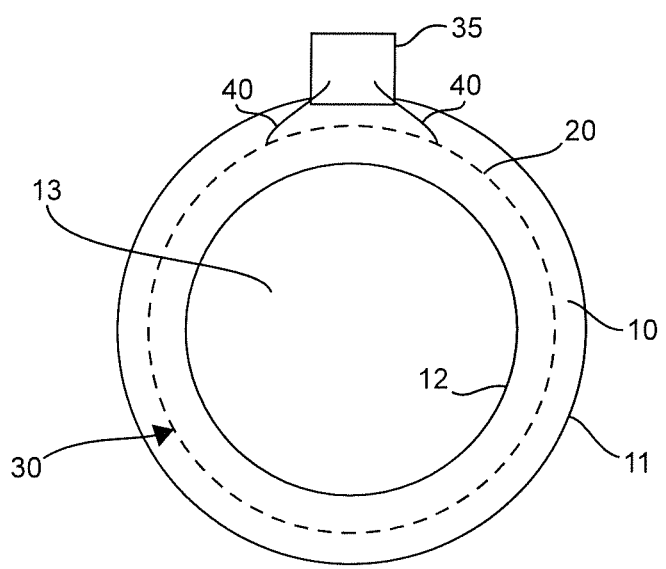
FIG. 1A-F. Schematic presentation of A, top view of an exemplary sensor as disclosed herein; B and C, cutaway cross-sectional views of exemplary sensors; D and E, schematics of alternative sensor designs; F, schematic of a wearable garment with a sensor disposed therein.

The present disclosure addresses the aforementioned issues regarding lactation parameter measurements by providing comfortable, easy to use wearable electronic device technologies. The devices comprise electrically conductive, non-volatile liquids embedded in a soft elastomeric body. These liquid conductors flow and deform with the soft elastomeric body to maintain their conductivity, and changes in their electrical properties due to such deformations (and other phenomena such as temperature changes) are detected and measured, e.g. as impedance. Significantly, the detection of changes is not uniaxial. Rather, the mechanical properties of the present devices allow them to conform to and sense changes in an underlying surface, such as a particular feature or portion of the human body, in a three-dimensional manner.

In some aspects, what is measured is the volume and temperature of a breast, for example, before, while, and after an infant nurses. Changes in breast volume and temperature lead to changes in sensor impedance through several mechanisms, including deformation of the embedded channels which contain conductive liquid, and cause changes in impedance, and temperature dependent variations in the ionic conductivity of the conductive liquid. Impedance changes are processed in a wide frequency range in conjunction with local measurements of, for example, the sensor temperature (through thermistors), breast volume change, breast temperature and a baby's suckling patterns, which are monitored accurately and simultaneously in real time. Measuring and quantitating these parameters, including comparing changes in the parameters to suitable control values, permits a user of the device to accurately track the changes in real time, and to store, retrieve and compare the parameters over time, enabling measurement of, for example, milk production in the breast, milk output during nursing, suckling activity and temperature changes of breast tissue.

The sensors advantageously detect volume changes (e.g., of as small as 1 mL), mechanical disturbances (e.g., suckling) and temperature variations within the physiological range. The mechanism behind sensing different stimuli generally depends on the variation of various electrical properties of the sensor affected by the sensor design and the presence of a grounded conductive structure with which the sensor is in contact. The sensor frequency response can be tuned through strategic design of the sensor or incorporation of additional sensors (e.g. thermistors) in the same circuit. This property has been exploited to isolate the measurements of different stimuli from each other. Further, in some aspects, the sensor design is tuned to provide an antenna-like behavior in which the human body serves as the ground plane. Such aspects are exploited to realize wireless sensing of the sensor behavior change.

In the wireless configuration, the sensor can be integrated with on-board electronics consisting of an impedance analyzer (e.g. Analog devices AD5933) to perform the impedance measurements, a wireless transmitter (e.g. Microchip RN4870) to transmit the data to a remote device, a logic component (any microcontroller, FPGA or DSP interface) to execute the signal processing schemes and a power source such a battery. Such a system can communicate with any mobile device or computer through various wireless protocols such as Bluetooth to enable continuous monitoring of the breast volume, suckling and temperature by the user. In this implementation, the electronics can be embedded in a stiff portion of the bra such as the straps or the gore.

Figure 1B:
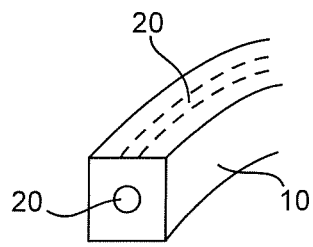
Figure 1C:
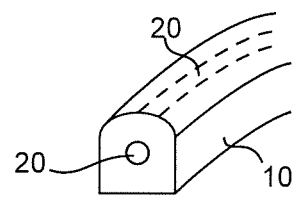
Figure 1D:
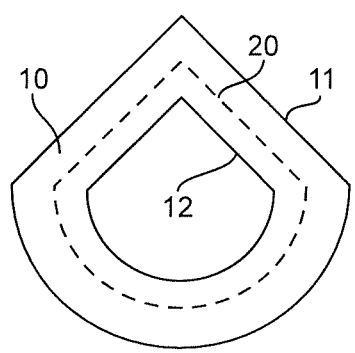
Figure 1E:
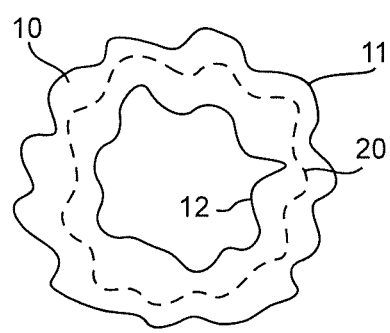

In general, the sensors have the shape of a closed band or loop, e.g. the two-dimensional structure thereof having a continuous surface (with no obvious beginning or end) which surrounds or defines an interior or central open space. Schematic representations of exemplary disclosed sensors are shown in FIGS. 1A-1D. FIG. 1A shows a one-dimensional top view of a sensor 10 that is substantially circular in shape and having outer edge 11 and inner edge 12, inner edge 12 defining a central open space 13. During use, sensor 10 would be fitted over and against the outer periphery of a breast and an inner portion of the breast would protrude through open space 13 to allow an infant to access the breast and nurse, i.e. at least a portion of the breast, and usually the entire breast, is circumscribed or surrounded by the sensor. As can be seen, channel 20 (shown in phantom) which contains an electrically conductive, non-volatile liquid, is embedded within sensor 10. FIGS. 1B and 1C provide cut away, cross-sectional side views through sensor 10 showing channel 20 embedded (encased, enclosed, etc.) therein, the channels having differing outer topologies (flat vs curved). The sensors themselves may be any of a variety of suitable shapes and sizes to accommodate the manufacturing process and the anatomy of the user, e.g. with various geometric and/or irregular borders. For example, FIGS. 1D and 1E depict exemplary non-circular sensors with non-circular borders. The portion of the sensor that is closest to the skin of a user is generally substantially flat to insure maximum contact between the sensor and the subject's skin (generally indirectly via a fabric in which the sensor is enclosed). The outer edges of the sensor may also contain flaps or extensions (not shown) to facilitate incorporating or anchoring the sensor into or within a wearable garment, for the attachment of electrical connections, etc.

Figure 1F:
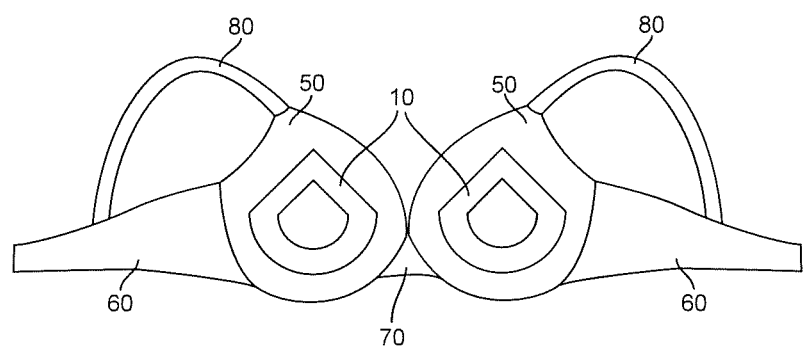

In some aspects, a sensor or sensors are incorporated into a wearable garment. For example, FIG. 1F shows a schematic representation of the interior (the part that is next to the body when worn) of an exemplary wearable garment comprising sensors. In this example, the garment is a "bra" which incorporates at least one, and usually two sensors, one in each cup. What is shown is cups 50 which each comprise a sensor 10, wings 60, gore 70 and straps 80.

Any suitable method may be used to attach or otherwise secure the sensors into a wearable garment. For example, the fabric of the garment may be layered and the sensor may be placed between layers of fabric. The sensors may be present in a preformed "pocket" of the garment, or the sensors may be sewn, glued, hooked, etc. into place between the layers of fabric. The sensors may be "built into" the garment so that they are connected directly to an edge of the fabric of the garment in a continuous manner, i.e. the sensor and the fabric of the garment form a substantially continuous surface which may also include small areas of overlap at the edges of the sensor to attach the sensor, e.g. by gluing, sewing, or by another suitable means. In some aspects, the sensor(s) is/are advantageously attachable and detachable from a wearable garment (e.g. such as a nursing bra) so that the wearable garment can be laundered separately.

Alternatively, the sensor may be a standalone device which is positioned by the user and held in place by a suitable mechanism. For example, the sensor(s) may be held in place by one or more straps, and/or by pressure exerted by a garment that is worn over the sensor to secure it in place, etc. Such standalone versions of the sensor may be covered with fabric.

Composition of the Sensors

The sensors disclosed herein are formed or made from material that are stretchable (elastomeric). In addition, the material may be soft, flexible, etc. so as to provide comfort to the user while worn. However, the materials are also suitable for molding so that the sensors encase (enclose, surround, etc.) channels to contain ionically conductive liquid and/or other elements (e.g. wires, thermistors, connectors, etc.) necessary to operation of the sensor; as well as for permitting electrical signals to be transmitted to and from the embedded ionically conductive liquid and/or other elements. The materials are generally elastomeric polymers. Examples of materials suitable for making the sensors include but are not limited to silicone rubbers and urethane rubbers or any elastomeric material with Shore hardness less than 00-50.

The disclosed sensors generally have a thickness of from about 2 mm to about 10 mm, and a thickness of from about 2 mm to about 5 mm is generally preferred. In addition, the width of a sensor (e.g. the distance between outer edge 11 and inner edge 12, as shown in FIG. 1A) is generally from about 5 mm to about 20 mm, and a width of from about 10 mm to about 15 mm is generally preferred. The perimeter of an outer edge of a sensor (e.g. outer edge 11) is generally in the range of from about 150 mm to about 500 mm and a perimeter of from about 200 mm to about 350 mm is generally preferred. The length of an inner edge of a sensor (e.g. inner edge 12) is generally in the range of from about 100 mm to about 400 mm and a length of from about 200 mm to about 300 mm is generally preferred.

Those of skill in the art will recognize that these values may change from device to device. For example, if the outer and inner edges of the sensor are irregular, then the lengths of the edges will be greater than with regular edges. In addition, the sensors can be differently sized to fit the purpose, e.g. to fit the breast size of the user, e.g. as small, medium, large, etc., or numerically sized (as for conventional bras such as 34, 36, 38, etc. with an indication of suitable for A, B, C, etc. sized cups). Alternatively, the sensors can be custom sized, made and adapted for an individual user who provides specific measurements.

The sensors comprise sensor elements which are enclosed (i.e. not open) channels filled with an ionically conductive liquid. The channels are embedded in the sensor i.e. they are surrounded by, encased within, etc. the material of which the sensor is made. Generally, the channels are within a distance of from about 0.5 to about 2 mm of an interior or inner surface of the sensor, (considering the cloth or fabric layer in between the sensor and the skin of a user) i.e. the surface of the sensor that is closest to the body of the user when worn; and within a distance of from about 1 mm to about 4 mm of an exterior, top or outer surface of the sensor, i.e. the surface of the sensor that does not face the body of the user when in use. The channels may extend around the entire sensor body or only around a portion thereof. In addition, channel 20 may be of any desired three-dimensional shape, e.g. substantially circular, angular, square, rectangular, trapezoidal, irregular, V-shaped, etc. as desired. The volume of a channel is typically in the range of from about 20 to about 200 mm$^3$, and is usually in the range of from about 50 to about 100 mm$^3$.

The embedded channels contain a non-volatile, electrically conductive liquid. The material of the sensor and the conductive liquid are selected so as to be inert with respect to each other, e.g. the conductive liquid does not dissolve the sensor material, does not leach into the sensor material and is generally not corrosive. Examples of suitable liquids that may be present in the sensors include but are not limited to any type of room temperature ionic liquids (RTILs) (e.g. 1-ethyl-3-methylimidazolium ethyl sulfate, 1-methyl-3-propylimidazolium bis(trifluoromethylsulfonyl)imide) or room temperature eutectic alloys of Ga (e.g. EGaIn or Gallinstan). The former provides higher sensitivity due the ionic nature of its conductivity leading to higher and frequency dependent impedances.

In some aspects, the ionic liquid is interfaced with external electronics through one or more, generally two, microelectrodes embedded in and/or otherwise attached to the sensor. The electrodes contact the conductive liquid and serve as electrical leads to connect the conductive liquid to external electronics. The connection may be made via an electronic interface or connector to which external electronic components can be attached ("plugged in") or detached, as needed. Both compliant and stiff electrodes can be interfaced with the conductive liquids. Compliant electrodes can extend into the deformable parts of the conductive liquid filled channels. Examples of compliant electrode materials include but are not limited to metal infused fabric threads, liquid alloys of Ga (EGaIn or Gallinstan), carbon-elastomer composites (e.g. carbon black, graphite, carbon nanotube or graphene filled elastomers). Rigid electrodes generally provide better interfacial conductivity; however, they cannot extend into the deformable parts of the conductive liquid filled channels. The sensor design can accommodate this feature by extending the channels to a rigid portion of the sensor where the conductive liquid interfaces with the electrodes. Examples of potential rigid electrode materials include metals widely used in electronics industry such as copper platinum, platinum-iridium, tungsten, gold or solders formed from alloys of two or more metals; or wire formed from alloys of two or more metals; etc. In addition, the electrodes may be silicon based, carbon fiber based, etc. FIG. 1A shows a schematic of electronic interface 35 to which electrode wires 40 are connected; electrode wires 40 also contact the ionic liquid in channel 20.

Temperature Detection

The disclosed sensors are not limited to detecting changes in volume. They are also advantageously capable of detecting/measuring and tracking the temperature of underlying tissue. This is useful because, for example, it is known that infections can cause temperature increases, and the ability to detect such changes, especially at an early stage, is very useful for treating or preventing a severe infection. For example, mastitis, such as lactation mastitis, refers to inflammation of the mammary gland, generally caused by a bacterial infection. This condition is very painful and early detection can facilitate management of the disease.

The temperature and changes in temperature of tissue underlying a sensor is detected by means of one or more temperature sensors embedded in or attached and electronically connected to the sensor. Examples of temperature sensors that may be integrated into the devices disclosed herein include but are not limited to: thermistors, thermocouples, fluoroptic probes, etc. such as those described in issued U.S. Pat. Nos. 9,724,154; 8,900,228; 8,814,428; 6,633,656; and 5,798,684; as well as published US patent applications 20170239139 and 20180049923, the complete contents of each of which is hereby incorporated by reference in entirety.

In some aspect, the temperature sensor is an electrical thermistor, i.e. a thermal resistor whose resistance is dependent on temperature. The resistance of a thermistor is altered by heating and cooling, and thermistors used in the practice of the invention are sensitive in the range of from about −25° C. to about 250° C. At least one thermistor, e.g. a micro- or miniature thermistor, is integrated directly into the body of the sensor (e.g. is embedded therein) or is attached to the body of the sensor. Thermistor 30 is depicted schematically in FIG. 1A.

Signal Detection, Processing and Output

Working Principle

Figure 3A:
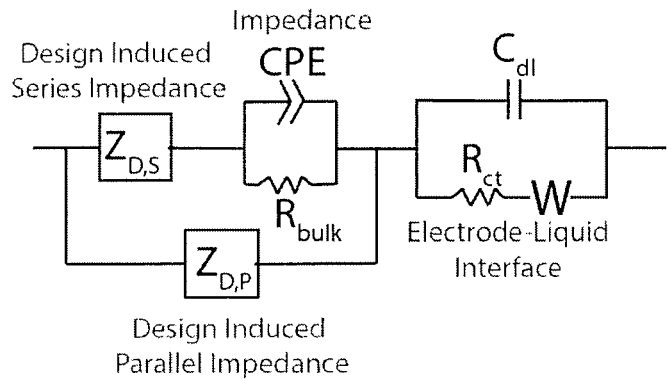
FIGS. 3A and B. A, general circuit model of the sensor element. B, various integration schemes considered for simultaneous volume and temperature measurements.

When the sensor conforms to the breast, changes in the breast's shape due to milk output or production, suckling and temperature lead to variations in the sensor's electrical impedance. This change is monitored by measuring the impedance of the sensor under AC excitation, and changes in impedance are correlated to the phenomenon that is being measured. A generalized circuit model representing the sensor element is shown schematically in FIG. 3A. This circuit includes of several distinct elements: first, the bulk impedance of the ionic liquid is in general represented by a resistor and a constant phase element (imperfect capacitor) [10] connected in parallel; second, the interfacial impedance between the electrodes is represented by a Randle's circuit incorporating the double layer capacitance, charge transfer resistance and the diffusion phenomena [10], [11]; and third, the particular design of the sensor induces additional electrical behavior similar to that of a combination of passive components such as inductors, resistors, capacitors or antennae, as demonstrated for other soft circuit components in the literature [12]. The electrically conductive human body acts as a ground plane for the sensor element, affecting its electromagnetic and thus electrical behavior, particularly at high excitation frequencies. Changes in the breast shape or temperature, or the amount of milk it includes, induce changes in one or more (e.g. all) of the electrical elements listed above. These changes are monitored through the AC impedance change of the sensor, from which the physical phenomena can be quantitatively inferred, provided that the appropriate sensor calibration is performed. Three possible sensor design and signal processing schemes can be used to achieve this goal. In all three schemes, the sensor impedance is first measured as a function of frequency (frequency response) using an impedance analyzer circuit. Next, the sensor's frequency response is fitted with an equivalent circuit model that best represents the sensor behavior, revealing the corresponding circuit component values. Third, physical variables such as breast volume and temperature are calculated using the circuit component values and the calibration functions that correlate such values to the corresponding physical variables. The calibration functions are obtained by measuring the sensor frequency response at various temperature and breast volume levels. During the calibration, a thermistor (temperature sensitive resistor) is used to benchmark the sensor temperature.

Figure 3B:
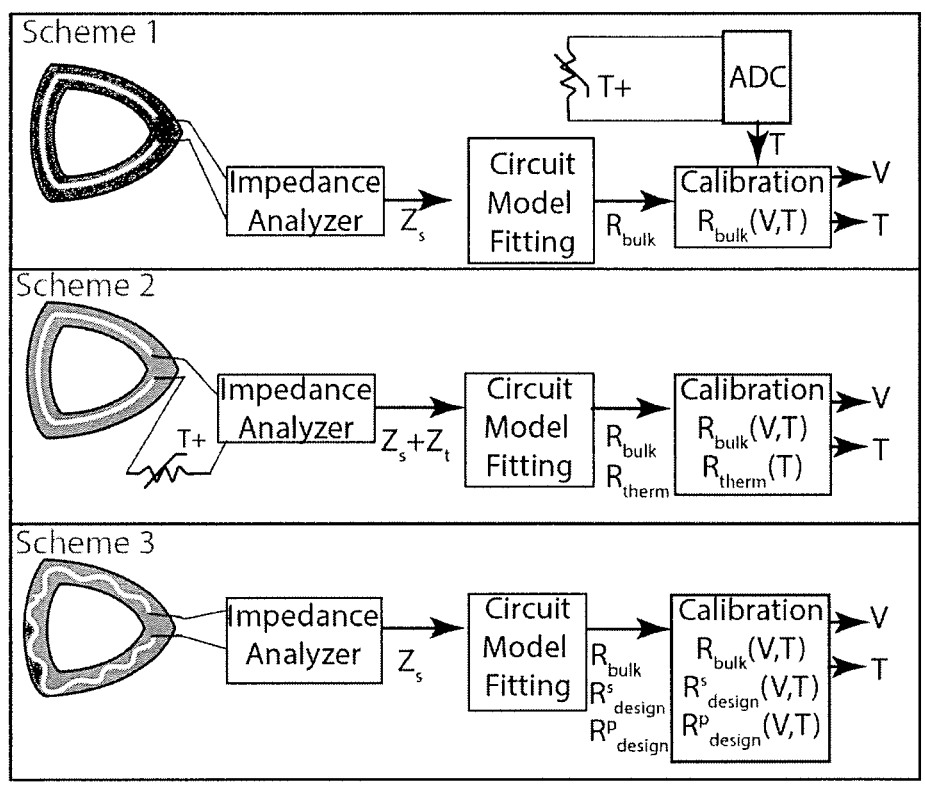

FIG. 3B provides a schematic illustration of three exemplary schemes for arranging the circuits of the sensors. In Schemes 1 and 2, the thermistor (or multiple thermistors across the sensor surface) is used in conjunction with the sensor during the measurement. These schemes are used when both volume and temperature variations affect only the bulk resistance of the sensor and do not lead to significant variations in any other circuit characteristics. In such a case, the sensor signal by itself does not provide sufficient information for simultaneous measurement of volume and temperature. In Scheme 1, the thermistor reading is used to independently measure the temperature which is inputted to the calibration function to accurately determine the volume. In Scheme 2, the thermistor is connected in series to the sensor, thus combining the two impedances. Here, the sensor bulk impedance varies with both temperature and volume and the thermistor impedance varies with temperature only, thus providing enough calibration parameters to simultaneously measure temperature and volume.

In Scheme 3, no thermistor is used and the sensor is strategically designed to tune the design induced impedance such that multiple circuit elements vary with temperature and volume, providing a sufficient number of calibration parameters for simultaneous temperature and volume measurements.

Among these schemes, Scheme 1 is likely to provide the highest accuracy while requiring the most amount of hardware. Scheme 2 reduces the required measurement and signal processing hardware, while increasing the complexity of the measurement and calibration algorithms for a similar level of accuracy. Scheme 3 minimizes the hardware use requiring only the sensor; however rigorous, complex calibration is required as is robust sensor behavior.

As a beneficial arrangement, the sensor can be interfaced with a small-scale electronic device capable of performing signal processing. Commercially available or custom designed Digital Signal Processing (DSP) boards can be used for this purpose. The measurements obtained by the sensors can be output, accessed, viewed, stored and tracked over time using any suitable computerized device or display. For example, sensor output may be output to or integrated with a small, hand-held device specific for the purpose, or with an existing computer program or application (e.g. a "health app") that is suitable for use e.g. with a PC, a cell phone, watch, bracelet, etc. The results can be displayed in any suitable manner, e.g. as graphs, tables, numerically, etc. In addition, "alarms", "warnings" or "timers" may be included e.g. to alert the user when the temperature of breast tissue is above normal, when a particular amount of milk has been expelled from the breast, when an infant has stopped suckling, etc. Further, the sensors can also measure and record time such as the length of a nursing session, or the time between nursing sessions, etc.

Making the Sensors

The sensors disclosed herein are made by any suitable process. In some aspects, a mold casting process is used; however, other methods of fabricating the sensors are not excluded.

In a molding method, a suitable mold is prepared (e.g. via 3-D printing, by mold casting, or by any other suitable means), a liquid precursor is introduced into a hollow cavity of the mold and allowed to harden (cure) into the desired shape, and the cured shape is removed from the mold. In some aspects, the molding of a sensor is (at least) a two-step process in that a first portion of the sensor having open geometry (e.g. open channels are present therein) is produced separately, and a second portion of the sensor e.g. a sealing layer, is cast separately from the first portion. The second portion is then connected or joined (e.g. glued) to the first portion in a manner that encloses the open channel, forming a 3-dimensional enclosed void or channel within the sensor.

Figure 2A:
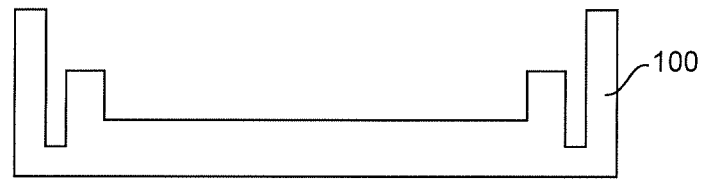
FIG. 2A-D. Prototype. Fabrication of a sensor. A, exemplary mold for forming a sensor; B, exemplary mold with liquid precursor for forming a sensor; C, cured bottom part 115 of sensor removed from mold; top part 120 of sensor shown as attached to cured bottom part 115 of sensor. Channel 125 is also depicted as a void between the top and bottom parts of the sensor.
Figure 2B:
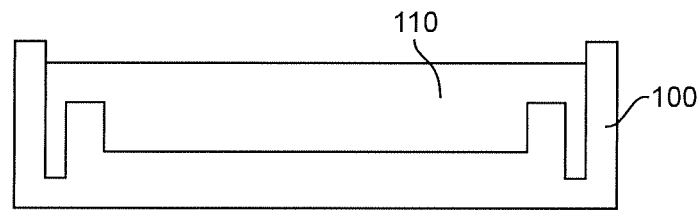
Figure 2C:
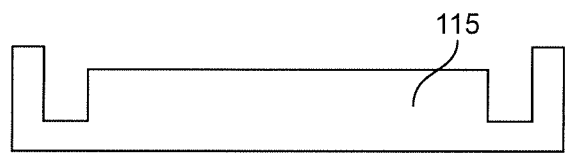
Figure 2D:
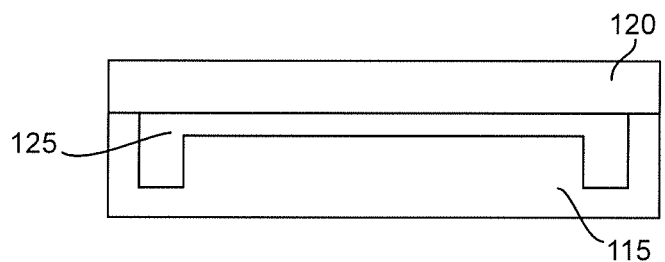

This process is illustrated schematically in FIGS. 2A-D, where FIG. 2A depicts mold 100, FIG. 2B depicts mold 100 containing liquid precursor 110, FIG. 2C depicts sensor portion I 115 that has been removed from mold 110, and FIG. 2D depicts sensor portion I 115 with sensor portion II 120 positioned thereon, thereby defining channel 20.

The enclosed channel is subsequently filled with a conductive liquid, e.g. via a needle or other very narrow conduit that pierces the sensor and expels the liquid into the channel. In some aspects, a suitable conduit (e.g. very narrow tubing) can be built into the sensor prior to filling, e.g. by gluing it in place when the top and bottom portions of the sensor are adhered to each other, and later plugged with a suitable material. Preferably, the sensor channels are filled in a manner that prevents the introduction of air bubbles, e.g. the liquid is degassed under vacuum prior to use. In fact, the entire filling procedure may be done with as much of the requisite equipment being under vacuum as possible.

It is noted that other components of a sensor, e.g. connectors, thermistors, electrodes, etc. are introduced into the sensor by any suitable means. For example, they may be attached (e.g. glued) onto or within the sensor, or built in e.g. introduced before the liquid precursor enters a mold so that the precursor cures around the item; or cemented (fully or partially) between the two portions of the sensor when the two portions are cemented together, etc.

Uses

In some aspects, the sensors disclosed herein are used to measure and/or monitor (on an ongoing basis or over a defined time period), the volume and/or temperature of an area of interest, usually a body part or portion, e.g. a breast. The results provided by the sensors and wearable devices or garments disclosed herein may be used by individuals for their personal information. Alternatively, the results can be transmitted (periodically or continuously) to a health care monitoring system such as those employed by physicians' offices, hospitals, etc. Such devices may be especially useful in hospital facilities where care is provided to women who have recently given birth. In particular, the devices monitor changes in breast volume in response to nursing, activity and as such provide indirect but highly correlated information about infant behavior, e.g. volume of milk that is imbibed, frequency and strength of the suckling reflex, etc. This can be especially beneficial if infants are born prematurely, and/or if either the mother or the infant have health conditions that impact nursing. For example, a physician monitoring information provided by the sensor may recommend that the infant's or the mother's diet be supplemented with additional nourishment or liquid, or that it is safe to discontinue supplements, that an infant is or is not ready to be discharged from a hospital, etc.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural references unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Sensor Design and Fabrication

Figure 4A:
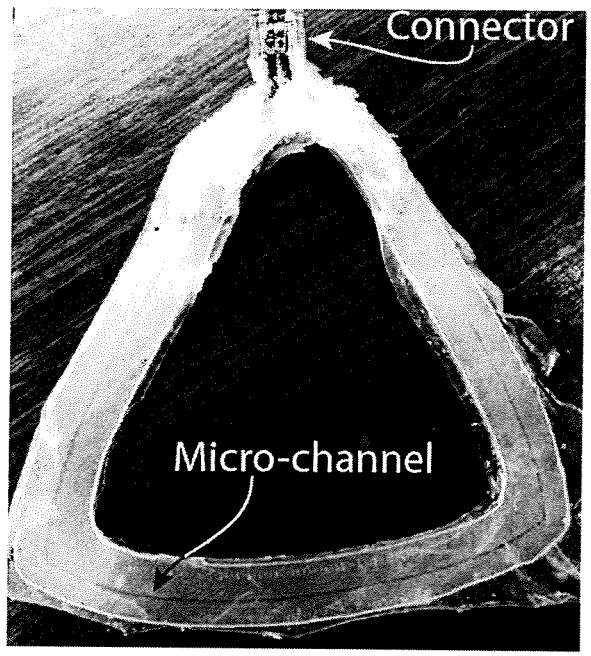
FIGS. 4A and B. A, prototype of an exemplary embodiment of a sensor; B, testing setup showing various components.

FIG. 4A depicts a prototype of a sensor as described herein. As discussed above, the fabrication process is shown schematically in FIGS. 2 A-D. For this example, the main sensor body including the channels was fabricated through casting of a platinum cured silicone (Eco-flex™ 0010, Smooth-On Inc.) into 3D-printed molds. The mold was printed out of polylactic acid (PLA) through fused deposition using a desktop 3D-printer (Felix Pro 1). The liquid silicone precursor was first poured into the master mold and cured at room temperature for four hours. The cured silicone body was then removed from the master mold and sealed with a preformed flat layer of the same silicone by applying a thin bonding layer of the precursor in between. Upon curing of the bonding layer, silver infused threads were inserted and the ionic liquid was injected into the channels. The injection process started with insertion of a syringe needle connected to an ionic liquid filled syringe barrel. The sensor and the barrel were then placed in a vacuum chamber and any trapped air inside the ionic liquid and the channels was removed (via the vacuum). The connection points between the silver threads and the sensor elements were then sealed with a silicone glue (Sil-Proxy™, Smooth-On Inc.).

1-ethyl-3-methylimidazolium ethyl sulfate and 1-methyl-3-propylimidazolium bis(trifluoromethylsulfonyl)imide have both been successfully used as the ionic liquid.

Testing Approach

Figure 4B:
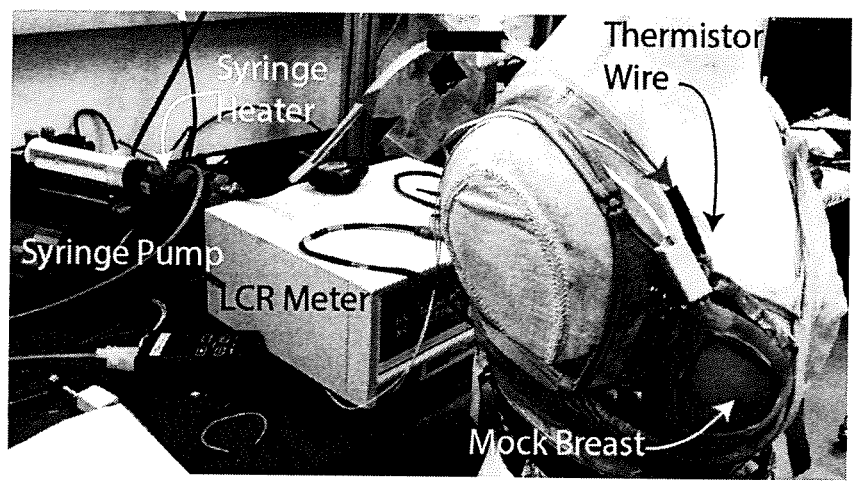

To test the capability of the sensor to measure volumetric and temperature changes of the breast, we constructed a mock-mother setup as shown in FIG. 4B. A mannequin torso was fitted with a water-filled silicone pouch mimicking the breast and the sensor was attached to the pouch. This pouch was connected to a 150 mL syringe controlled by a precision syringe pump. This syringe was also instrumented with a syringe heater to control the water temperature. The syringe pump infused and withdrew controlled (measured) amounts of water into the mock-breast thus emulating volumetric changes of the breast. Similarly, the heater temperature was tuned in conjunction with water circulation through repeated infusions and withdrawals to obtain the desired breast temperature. Two thermistor elements were integrated on the mock-breast with the sensor. The sensor impedance was measured through an LCR meter and kelvin probe. One of the thermistors was used for the benchmark temperature measurements in the implementation of all the schemes. That thermistor was connected to a fixed resistor in series and the entire circuit was excited by a 5 V DC signal. The thermistor was also connected to the analog-to-digital converter of a data acquisition system which measures the potential drop. The drop is linearly proportional to the temperature with the calibration functions available from the thermistor manufacturer. The benchmarking thermistor was the only thermistor used in Schemes 1 and 3. For Scheme 2, another thermistor was connected in series with the sensor and the LCR meter was connected to both the sensor and the thermistor, instead of only to the sensor.

In the testing procedure, first, the "breast size" was set by filling the pouch to an initial volume prior to connecting it to the pump. Then the water-filled syringe was heated up to 100° C. using the syringe heater. It should be noted that the water temperature inside the syringe-tube-pouch line is significantly lower due to heat transfer with the ambient atmosphere. For each data point, hot water was infused and withdrawn several times until the desired temperature was stably monitored by the benchmark thermistor at the desired infused volume. Finally, the sensor impedance was measured at a frequency range of 1 kHz-100 kHz by incrementing the frequency by 1 kHz and recording the real and imaginary values of the sensor impedance at each increment. This procedure was repeated for five different infused volumes (0, 30, 60, 90 and 120 mL) and at six temperatures (28, 30, 32, 34, 36 and 38° C.).

The frequency dependent impedance data that was obtained was post-processed to fit an impedance model corresponding to an equivalent circuit consisting of resistors and capacitors, the exact form of which depended on the scheme used. The variation of the circuit component values with respect to volume and temperature were then determined.

Results and Discussion

This section summarizes the results of the test procedures described above and the implementation of the three operation schemes along with their accuracy evaluation.

Scheme 1:

For testing of the sensor operating according to Scheme 1 of FIG. 3B, we utilized a sensor design that comprises a single channel with dimensions 0.5 mm by 0.6 mm and extending between the two leads of the sensor and around the entire sensor body. The Nyquist plots representing the impedance of the sensor constant temperature (32° C.) with varying infused volumes and with a constant infused volume (60 mL) while varying the temperature, are given in FIGS. 5B and C, respectively. The impedance variation with frequency is best represented by a RC-R circuit depicted by FIG. 5A, as determined by least-squares regression of the data that was obtained ($R^2 > 99\%$). Here, the resistor and capacitor in parallel can be visualized as the combination of the bulk sensor impedance and the design induced impedance. The series resistor likely corresponds to the interfacial impedance between the silver thread electrodes and the ionic liquid.

Figure 5A:
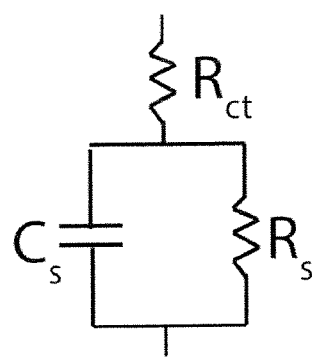
FIG. 5A-E. A, equivalent circuit model for the sensor in Scheme 1, B; Nyquist plot of the sensor impedance at constant temperature of 32° C. and varying infused volume levels; C, Nyquist plot of the sensor impedance at constant volume of 60 mL and varying temperatures; D, variation of the bulk sensor resistance with volume at various temperatures; E, variation of the bulk sensor resistance with temperature at various volume levels.
Figure 5B:
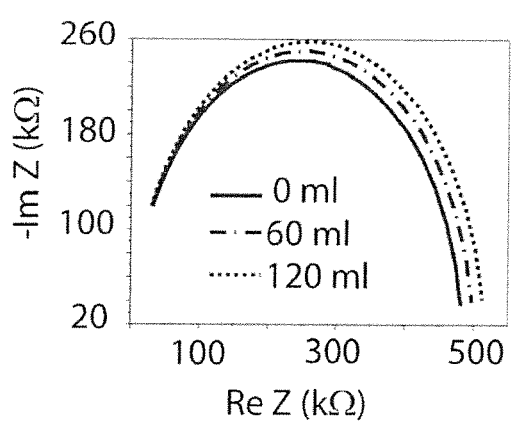
Figure 5C:
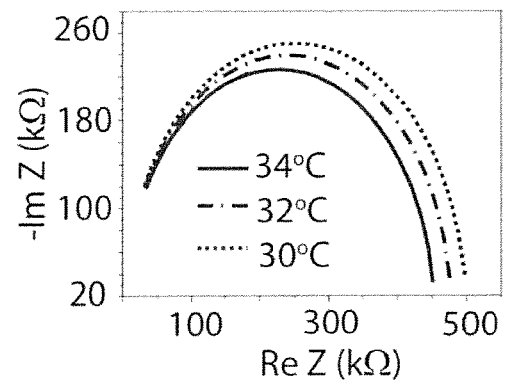
Figure 5D:
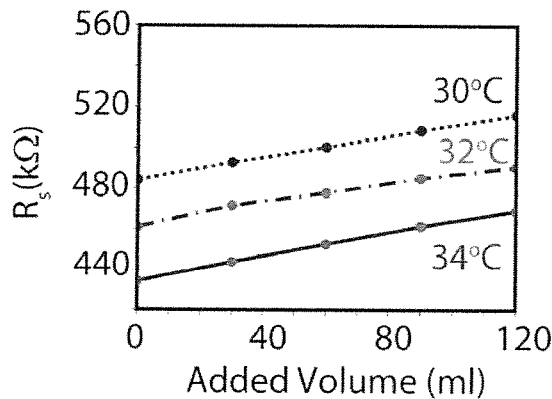
Figure 5E:
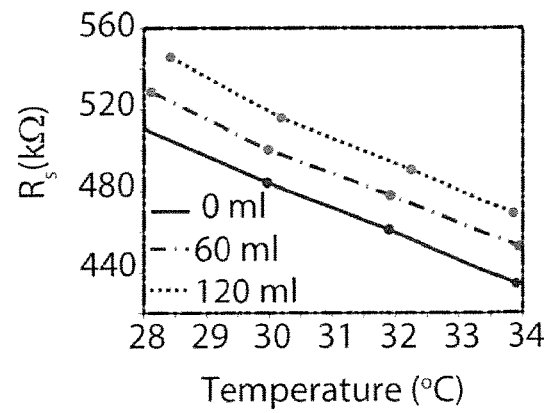

FIG. 5D shows the variation of the bulk sensor resistance with the infused volume at various constant temperature levels. Similarly, FIG. 5E shows the variation of the bulk resistance with temperature at various infused volume levels. As can be seen, the resistance varies linearly with both the infused volume and the temperature, when the one of the variables is kept constant as shown. The temperature dependence of the resistance can be correlated to the commonly observed increase in the inherent conductivity of the ionic liquids with increasing temperature [13], whereas the volume sensitivity can be associated with the change of the microchannel length and cross-section as a result of the sensor deformation. The resistance of a given conductor is given by:

$$R = \rho \frac{l}{A} \quad (1)$$

where $\rho$ is the inherent resistivity of the material and l and A are the length and cross-sectional area of the conductor, respectively. The results show that the inherent resistivity is a linear function of temperature ($\rho(T) = aT + b$) where T is the breast temperature and the length-area ratio is a linear function of volume $$\left(\frac{l(V)}{A(V)} = cV + d\right),$$

where V is the infused volume. Accordingly, Eq (1) becomes:

$$\begin{aligned} R(T, V) &= \rho(T) \frac{l(V)}{A(V)} \quad (2) \\ &= (aT+b)(cV+d) \\ &= cbV + adT + acVT + bd \end{aligned}$$

Figure 6A:
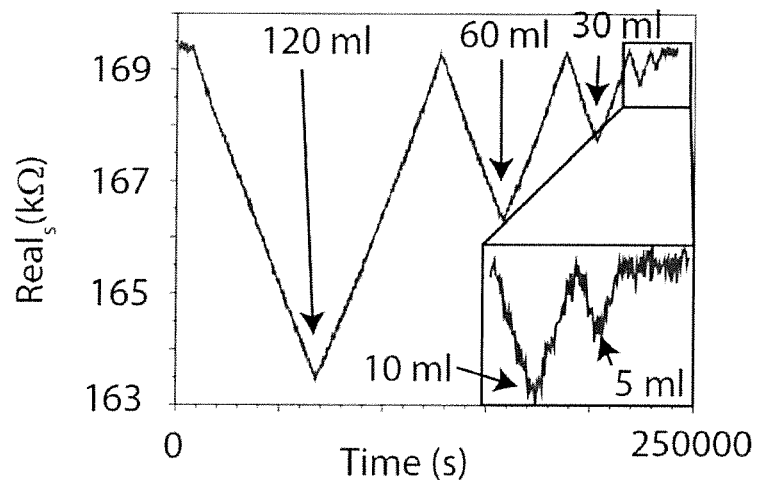
FIG. 6A-C. With reference to Scheme 1, A, variation of the real component of sensor impedance at constant temperature during infuse and withdraw cycles; B, accuracy of the volume predictions for 4-point calibration; C, accuracy of the volume predictions for calibration with the entire dataset.

This equation describing a surface correlating the bulk resistance to temperature and volume is the calibration function of the sensor. For this particular sensor, the coefficients in Eq. 1 (calibration coefficients) are determined through least-square fitting ($R^2 > 99\%$) of the experimental data by cb=610.86, ad=−12698.33, ac=−9.96, bd=865088.66. It should be noted here that the cross-talk coefficient, ac, is rather small. In fact, the small cross-talk can also be observed in the experimental data. The rate of change of the resistance with volume at constant temperature is nearly constant, indicated by the nearly parallel lines shown in FIG. 5D. Similarly, the parallel lines shown in FIG. 5E also indicate that the rate of change of the resistance with temperature at constant volume is not a strong function of volume. These results have significant implications towards the operation of sensor. The small cross-talk between the temperature and volume renders the calibration surface nearly planar, which means that only a few calibration experiments are sufficient to calibrate the sensor. Furthermore, the fact that the resistance varies linearly with volume at constant temperature indicates that a given amount of relative volume change of the breast generates a constant signal variation regardless of the current breast volume or more importantly, size of the breast. As a result, personal calibration of the sensor may be unnecessary, provided that the breast temperature is continuously monitored. In fact, within short periods of time during which temperature changes are small, the volume changes can be monitored through the sensor impedance at a single frequency, as shown in FIG. 6A. As can be seen, the sensor impedance at 20 kHz is plotted as a function of time while various amounts of water are infused and then withdrawn at fixed rates, demonstrating the sensitivity of the sensor to an infused volume as small as 5 mL. As expected, the impedance change is linear with the changing volume.

According to Scheme 1 (FIG. 3B), the temperature of the breast was directly monitored through a thermistor. In that Scheme, the thermistor was connected in series with a constant resistor and the DC voltage drop across the thermistor was measured through a A/D converter to extract the current resistance value. This value was then analyzed using manufacturer supplied calibration functions of the thermistor to determine the temperature. For volume measurements, the real and imaginary part of the sensor impedance was acquired as a function of frequency. This data was used to determine the bulk resistance through fitting of the equivalent circuit model given in FIG. 5A. Volume was then determined via Eq. 2 given the measured temperature and the resistance values.

Figure 6B:
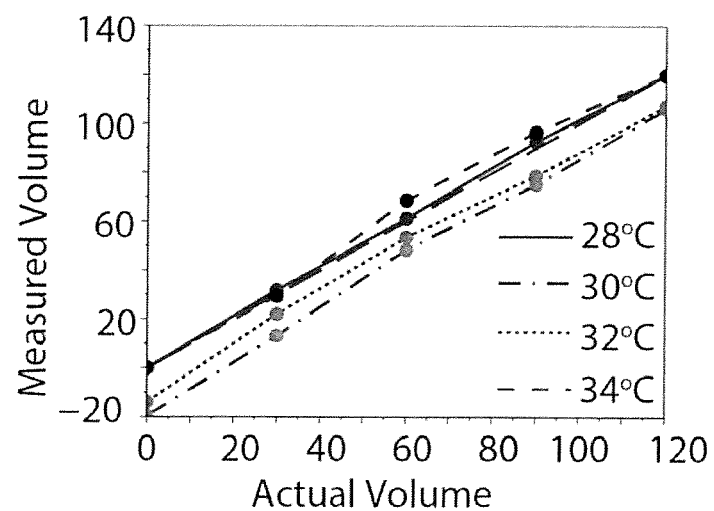

To assess the performance of this approach, a validation test was performed using the collected experimental data. In this assessment, only four data points, 0 and 120 mL at 28° C. and 34° C. were used to obtain the calibration function, and the rest of the data was input to the volume prediction scheme. The predicted and actual volumes were then compared. FIG. 6B shows the results of this test. Among the 20 data points tested in the 0-120 mL and 28° C.-34° C. range, the predictions had an average absolute volume error of 7.54 mL and a standard deviation of 6.5 mL. As shown, predictions at 30° C. and 32° C. were, on average, 13 mL less than the actual values. However, relative variation of the volume was accurately captured at constant temperature for these data sets. Considering the manner in which the experiments were conducted, e.g. that the data at different volumes were obtained back to back at a constant temperature to save time, these average shifts can be related to experimental errors such as trapped air inside the water circuit. It should be noted that these errors substantially skew the average error. In fact, if the predictions at 30° C. and 32° C. are shifted up by the 0 mL predictions on each temperature, mimicking a user "zeroing" the sensor, the average absolute error and standard deviation is reduced to 2.97 mL and 3.03 mL, respectively.

Figure 6C:
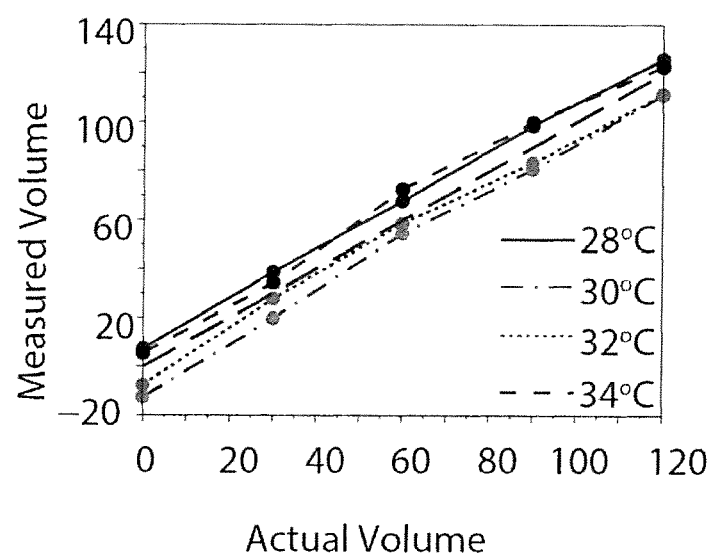

FIG. 6C shows the results of the predictions obtained by using the entire data set (instead of just four points as in FIG. 6B), both for calibration and validation. Using this approach, the mean absolute volume error was determined to be 7.29 mL with a standard deviation of 3.09 mL. When each data set obtained at constant temperatures are "zeroed" at 0 mL as described above, these values are 2.5 mL and 2.39 mL, respectively. The fact that full data calibration and 4 point calibration yielded very similar errors shows that in fact only a small number data points is sufficient to capture and calibrate sensor behavior in the volume and temperature ranges that were tested.

Figure 7A:
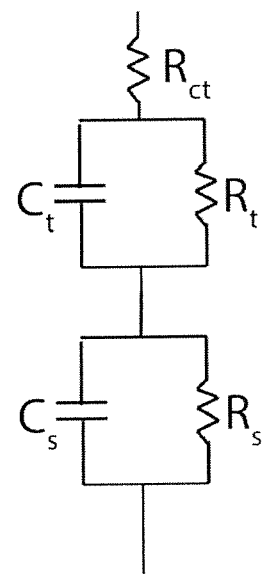
FIG. 7A-G. A, equivalent circuit model for the sensor+ thermistor in Scheme 2; B, Nyquist plot of the sensor-thermistor system impedance at constant temperature of 32° C. and varying infused volume levels; C, Nyquist plot of the sensor-thermistor system impedance at constant volume of 60 mL and varying temperatures; D, variation of the bulk sensor resistance with volume at various temperatures; E, variation of the thermistor resistance with volume at various temperatures; F, variation of the bulk sensor resistance with temperature at various volume levels; G, variation of the thermistor resistance with temperature at various volume levels.
Figure 7B:
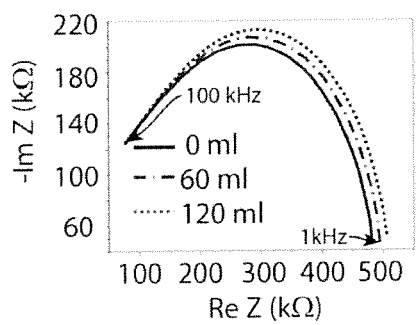
Figure 7C:
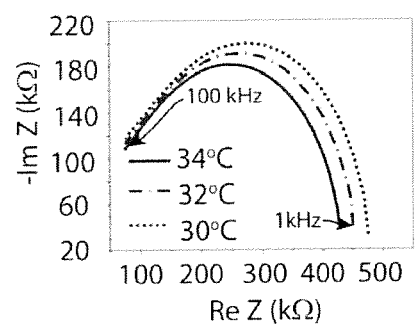
Figure 7D:
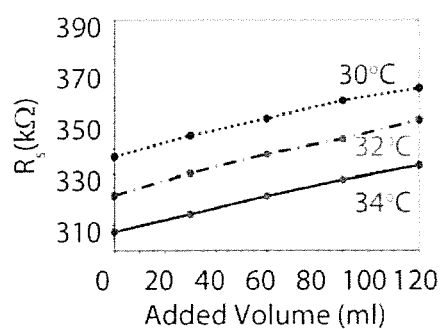
Figure 7E:
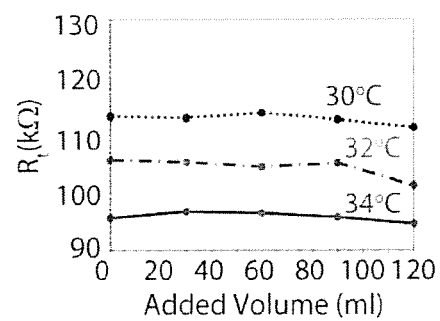
Figure 7F:
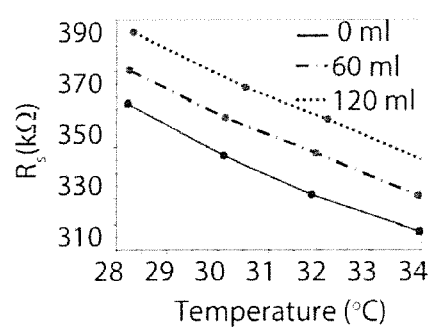
Figure 7G:
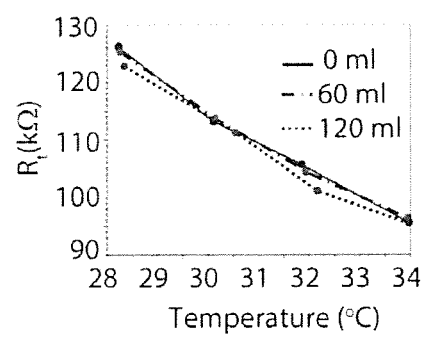

Scheme 2:

In Scheme 2, the sensor is connected in series with a thermistor as shown in FIG. 3B. In this Scheme, the circuit model is modified to add the resistive and capacitive contributions ($R_t$ and $C_t$) of the thermistor, as shown in FIG. 7A. It should be noted that even though the thermistor is a pure resistor under DC excitation, at high frequencies it also exhibits capacitive behavior, as is the case for any fixed resistor. The frequency dependent variation of the real and imaginary parts of the combined impedance under constant temperature and volume conditions are given in FIGS. 7B and C, respectively. In this case, the temperatures are measured using a second, benchmarking thermistor following the same approach explained above under Scheme 1. The bulk sensor resistance ($R_s$) showed a similar variation with volume and temperature as that which is shown in FIGS. 7E-G. For the particular sensor presented here, the calibration constants given in Eq 2 were determined to be cb=264.74, ad=−8793.09 ac=−0.83, and bd=602848.06, when the 4-point calibration approach is used. The thermistor resistance, on the other hand, is only sensitive to temperature in a linear fashion, as intended. The calibration function for the thermistor resistance is accordingly given by:

$$R_t = aT + b \quad (3)$$

For the particular thermistor used, the associated calibration constants were determined to be a=−5075.21 and b=268087.01.

Figure 8A:
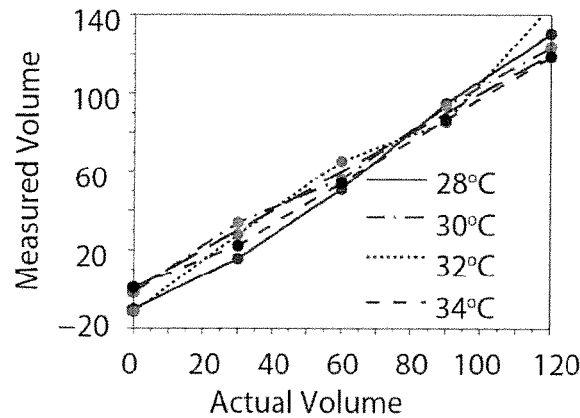
FIG. 8A-D. Scheme 2 results: A, accuracy of the volume predictions for 4-point calibration; B, accuracy of the temperature predictions for 4-point calibration; C, accuracy of the volume predictions for calibration with the entire dataset; D, accuracy of the temperature predictions for calibration with the entire dataset.
Figure 8B:
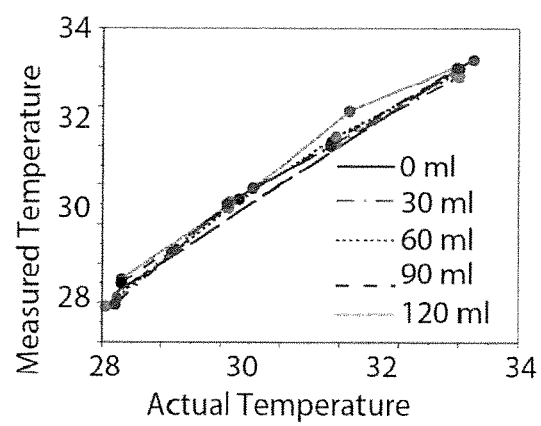
Figure 8C:
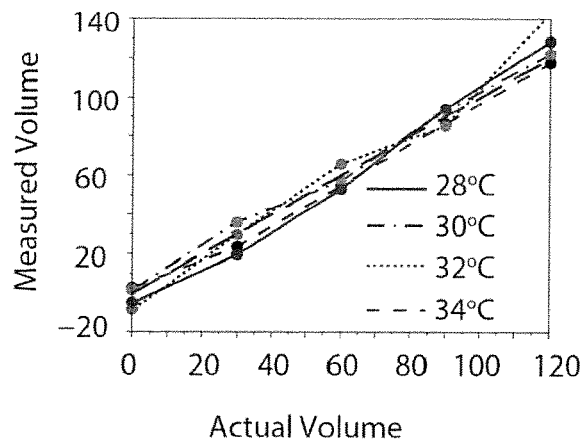
Figure 8D:
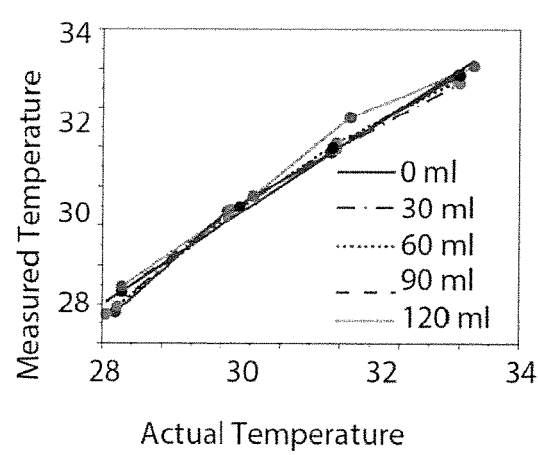

To assess the volume and temperature prediction accuracy of Scheme 2, the 4-point calibration approach highlighted above was used and the rest of the experimental data was used for validation. For the predictions, each data set was fitted with the circuit model given in FIG. 7A to determine $R_t$ and $R_s$. Next, the temperature prediction was calculated via Eq. 3 using the determined $R_t$ value. Eq. 2 was then used to determine the volume prediction using the calculated temperature and the determined $R_s$ value. FIGS. 8A and 8B show the results obtained regarding the accuracy of the volume and temperature predictions. The average absolute volume error with 4-point calibration is 6.63 mL with a standard deviation of 5.7 mL. When the data sets corresponding to various constant temperature levels were "zeroed" at 0 mL, the average absolute volume error and its standard deviation were reduced to 3.45 mL and 3.68 mL, respectively. The average absolute temperature error recorded with the 4-point calibration is 0.236° C. with a standard deviation of 0.165° C. FIGS. 8C and D show the predictions made by using the entire dataset for calibration. In this case, the average absolute volume error was 5.69 mL with a standard deviation of 4.83 mL. When the datasets were zeroed at 0 mL at each temperature, the average error and its standard deviation reduced to 2.78 mL and 3.54 mL, respectively. The average absolute temperature error in this case was determined to be 0.20° C. with a standard deviation of 0.15° C. These results show that Scheme 2 offers a level of accuracy and data linearity similar to that of Scheme 1, while reducing the complexity of the electronics that are used.

Scheme 3:

Scheme 3 (FIG. 3B) involves designing the sensor channels such that the combination of the bulk sensor impedance and the design induced impedance components provide sufficient information to determine both volume and temperature, without using a separate temperature sensor. Specifically, this is achieved if another circuit element other than $R_s$ is rendered sensitive to volume and/or temperature, providing a second calibration function, in addition to that of Eq 2 or in place of that of Eq 3.

Figure 9A:
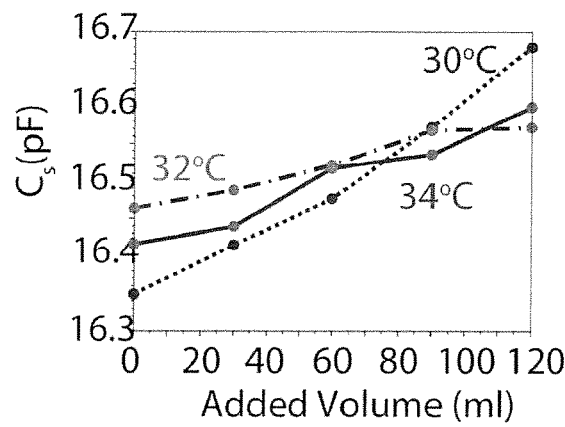
FIG. 9A-D. A, variation of sensor capacitance with volume at various temperatures; B, variation of sensor capacitance with temperature at various volume levels; C, accuracy Scheme 3 implementation in estimating volume; D, accuracy of Scheme 3 implementation in estimating temperature.
Figure 9B:
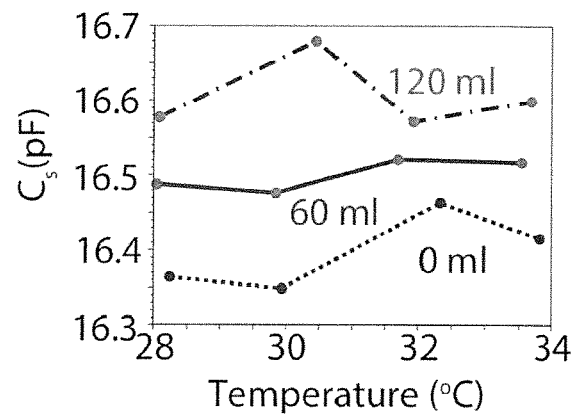

The feasibility of Scheme 3 is borne out in that some of the sensors in the more conventional one channel design, when measured under Scheme 1 configuration with the equivalent circuit model given by FIG. 5A, exhibited a capacitive component ($C_s$) that is sensitive to only volume, in addition to the sensitive bulk resistance. FIGS. 9A and B show the variation of this capacitance with varying volume and temperature, respectively. Here, the sensor capacitance is modelled as a linear function of the volume $$C_s = aV + b \quad (4)$$

Figure 9C:
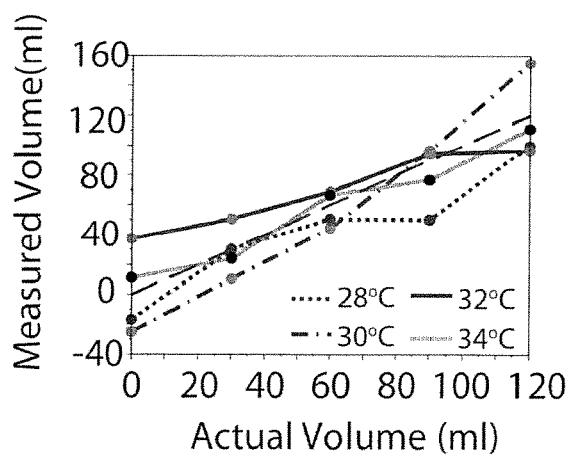
Figure 9D:
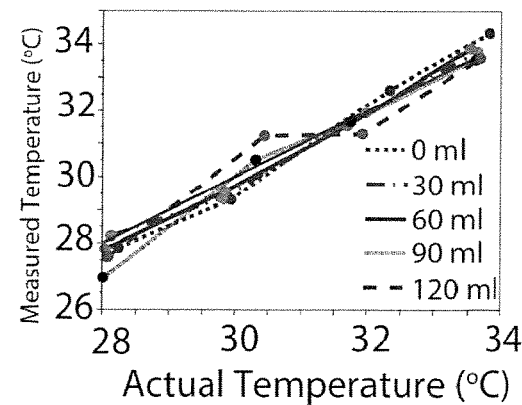

Basically, in this implementation of Scheme 3, Eq. 4 replaces Eq 3 in Scheme 2. The volume temperature estimation approach for Scheme 3, follows the same steps as Scheme 1 until the determination of the equivalent circuit parameters. At this point, Eq. 4 is used along with the determined $C_s$ and calibrated a and b values to estimate the volume. Next, this volume value is plugged in Eq. (2) to determine the estimated temperature. Here, no thermistor reading is utilized. FIGS. 9C and D show the volume and temperature estimates vs. the actual values. For these estimations, the absolute average volume error was determined to be 16.5 mL with a standard deviation of 11.3 mL. The average absolute temperature error was determined as 0.35° C. with a standard deviation of 0.27° C. When the datasets are zeroed at 0 mL at each temperature, the average absolute volume error and its standard deviation reduces to 10 mL and 9.89 mL, respectively. It should be noted that this demonstration does not fully represent the main idea behind Scheme 3, as $C_s$ is not purely a design-induced impedance component.

Example 2

Other Functionalities

Figure 10A:
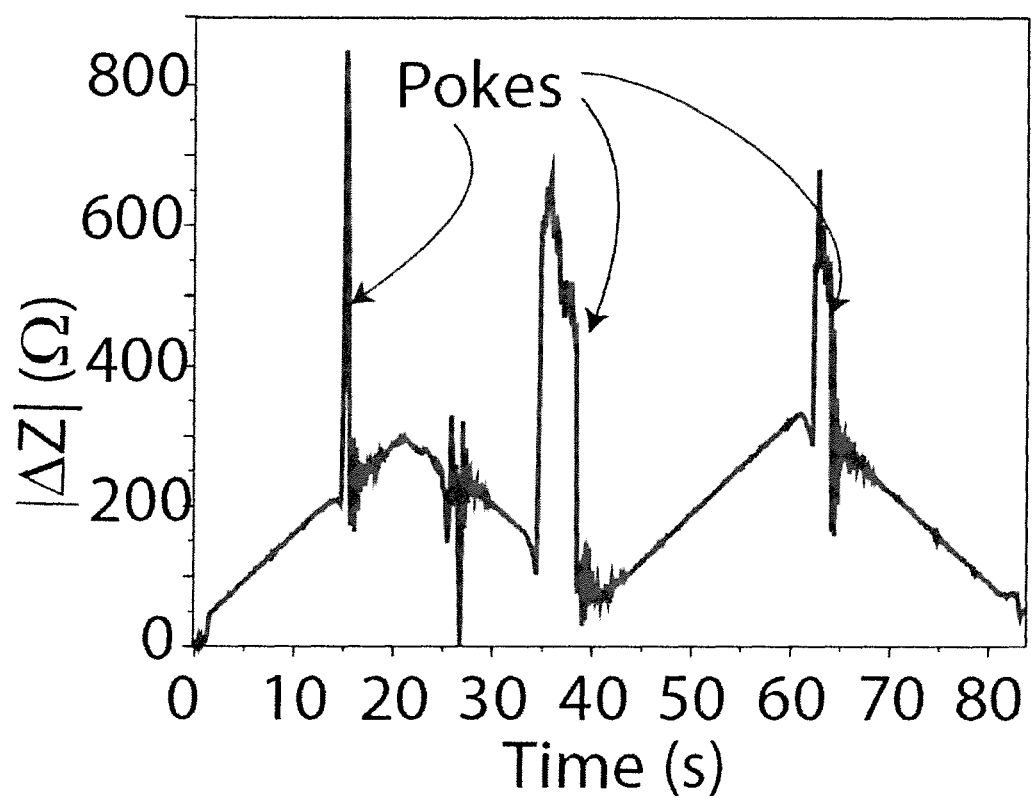
FIGS. 10A and B. A, response of the raw sensor signal to intermittent "pokes" during infuse-withdraw cycles; B, raw sensor signal when its worn by an individual.
Figure 10B:
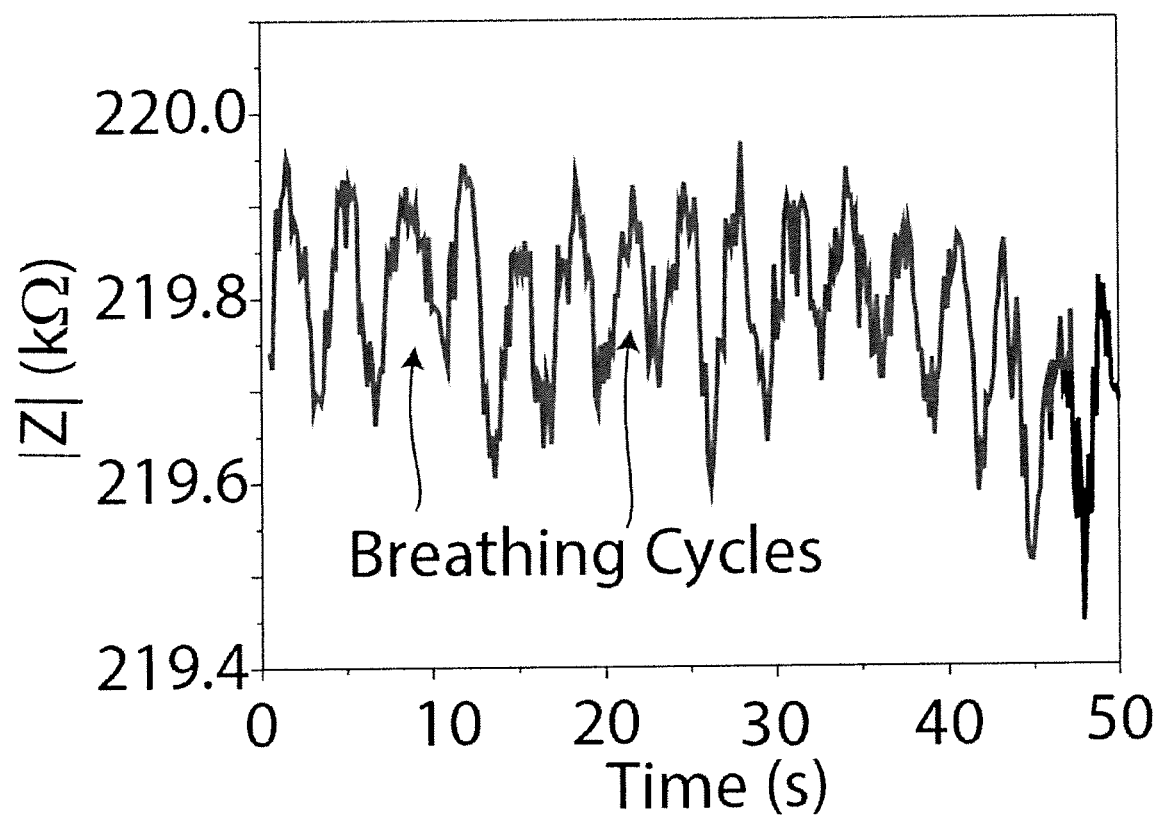

The sensor element in the disclosed devices is sensitive to changes in breast shape through which the volume information is inferred. The shape change resulting from other transient deformations such as baby's suckling, the mother's breathing etc. also result in changes in the sensor signal. FIG. 10 shows the raw sensor signal in two particular cases where such signal variations are observed. In FIG. 10A the mock breast is "poked" at the center briefly during infuse/withdraw cycles, emulating a suckling event. It should be noted that this is purely a transient effect and the signal recovers back to its original trend immediately thereafter. Accordingly, such effects are not expected to influence the long term volume measurements. FIG. 10B is the sensor data obtained when an individual wore the nursing bra to which the sensor element was attached. During this experiment, the individual stood still. The periodic oscillations in the signal were observed to coincide with the individual's breathing pattern. Such an effect can be advantageously used to monitor's a mother's breathing. However, to prevent this signal variation from affecting the volume measurements, two sensor elements on two breasts can be used. The non-nursing breast will exhibit the same signal variation due to chest expansion and contraction and thus can be used to subtract its effect from the signal coming from the nursing breast.

REFERENCES

[1] N. F. Butte, W. W. Wong, P. D. Klein, and C. Garza, "Measurement of milk intake: tracer-to-infant deuterium dilution method.," *Br. J. Nutr.*, vol. 65, no. 1, pp. 3-14, 1991.

[2] J. C. Kent, A. R. Hepworth, D. B. Langton, and P. E. Hartmann, "Impact of Measuring Milk Production by Test Weighing on Breastfeeding Confidence in Mothers of Term Infants," *Breastfeed Med*, vol. 10, no. 6, pp. 318-325, 2015.

[3] Kolberg, Eliezer, and Yitzhak Epstein. "Breast Milk Flow Meter Apparatus and Method." U.S. Pat. No. 8,280,493. 2 Oct. 2012.

[4] Binder, Adina. "Measuring Fluid Excreted from an Organ." U.S. patent application Ser. No. 12/776,023.

[5] H. Hafezi, M. Judith I. Feezer, D. A. Webb, "Breast Sense feeding monitor," Patent Application WO2018053045A2, 2017.

[6] S. E. Daly et al., "The determination of short-term breast volume changes and the rate of synthesis of human milk using computerized breast measurement," *Exp. Physiol.*, vol. 77, no. 1, pp. 79-87, 1992.

[7] Harari, Tzach, Liat Huller-Harari, and Shaye Kivity. "Breastfeeding Milk Consumption Measuring Device." U.S. Pat. No. 8,801,658. 12 Aug. 2014.

[8] Y. Menguc et al., "Wearable soft sensing suit for human gait measurement," *Int. J. Rob. Res.*, November 2014.

[9] J. Chossat, Y. Tao, V. Duchaine, and Y. Park, "Wearable Soft Artificial Skin for Hand Motion Detection with Embedded Microfluidic Strain Sensing," pp. 2568-2573, 2015.

[10] A. KARTHIKEYAN, P. VINATIER, and A. LEVASSEUR, "Study of lithium glassy solid electrolyte/electrode interface by impedance analysis," *Bull. Mater. Sci.*, vol. 23, no. 3, pp. 179-183, 2000.

[11] Y. N. Cheung, Y. Zhu, C. H. Cheng, C. Chao, and W. W. F. Leung, "A novel fluidic strain sensor for large strain measurement," *Sensors Actuators, A Phys.*, vol. 147, no. 2, pp. 401-408, 2008.

[12] A Fassler and C. Majidi, "Soft-matter capacitors and inductors for hyperelastic strain sensing and stretchable electronics," *Smart Mater. Struct.*, vol. 22, no. 5, p. 55023, May 2013.

[13] H. Ota et al., "Highly deformable liquid-state heterojunction sensors," *Nat. Commun.*, vol. 5, pp. 1-9, 2014.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A sensor comprising:
    a closed band of non-conductive elastomeric material having at least one sealed channel embedded therein, wherein the at least one sealed channel includes a non-volatile electrically conductive liquid;
    at least two microelectrodes in electrical communication with the non-volatile electrically conductive liquid; and
    a connector operatively coupled to the at least two microelectrodes and an external electronics system, wherein the connector transmits and receives electrical signals to and from the at least two microelectrodes and the external electronics system.

2. The sensor of claim 1, further comprising a temperature sensor.

3. The sensor of claim 1, wherein the external electronics system comprises an electronic device configured to perform signal processing.

4. A wearable garment for monitoring breast volume and temperature, comprising
    at least one cup having a contoured shape for engaging a woman's breast, wherein the at least one cup comprises at least one sensor according to claim 1.

5. The wearable garment of claim 4, wherein the at least one cup of the wearable garment comprises a sensor according to claim 1 and a second cup of the wearable garment comprises a control sensor that detects inhalation and exhalation.

6. A method of measuring breast volume and temperature in a subject in need thereof, comprising,
    positioning a sensor of claim 1 or a wearable garment comprising the sensor on a breast or breasts of the subject,
    measuring sensor impedance as a function of frequency to obtain a frequency response,
    determining circuit component values by fitting the frequency response with a circuit model that represents sensor behavior, and
    calculating breast volume and temperature using the circuit component values and predetermined calibration functions that correlate the circuit component values to corresponding physical variables for breast volume and temperature.

7. The method of claim 6, wherein the predetermined calibration functions are obtained by measuring sensor frequency responses at a plurality of breast volume and temperature levels.

* * * * *